(12) United States Patent
Skigen

(10) Patent No.: US 9,687,444 B2
(45) Date of Patent: *Jun. 27, 2017

(54) VETERINARY ACTIVE AGENT APPLICATION

(71) Applicant: Andrew L. Skigen, Jacksonville, FL (US)

(72) Inventor: Andrew L. Skigen, Jacksonville, FL (US)

( * ) Notice: Subject to any disclaimer, the term of this patent is extended or adjusted under 35 U.S.C. 154(b) by 244 days.

This patent is subject to a terminal disclaimer.

(21) Appl. No.: 14/229,166

(22) Filed: Mar. 28, 2014

(65) Prior Publication Data

US 2014/0286876 A1 Sep. 25, 2014

Related U.S. Application Data

(63) Continuation-in-part of application No. 13/732,408, filed on Jan. 1, 2013, now Pat. No. 9,192,572.

(60) Provisional application No. 61/806,779, filed on Mar. 29, 2013, provisional application No. 61/582,453, filed on Jan. 2, 2012.

(51) Int. Cl.

| | |
|---|---|
| *A61K 49/00* | (2006.01) |
| *A61K 9/00* | (2006.01) |
| *A61K 31/43* | (2006.01) |
| *A61K 31/7056* | (2006.01) |
| *A61K 31/545* | (2006.01) |
| *A61K 31/4164* | (2006.01) |
| *A61K 31/196* | (2006.01) |
| *A61K 31/47* | (2006.01) |
| *A61K 31/167* | (2006.01) |
| *A61K 31/245* | (2006.01) |
| *A61K 31/5375* | (2006.01) |
| *A61K 9/70* | (2006.01) |

(52) U.S. Cl.
CPC ............ *A61K 9/0056* (2013.01); *A61K 9/006* (2013.01); *A61K 9/7007* (2013.01); *A61K 31/167* (2013.01); *A61K 31/196* (2013.01); *A61K 31/245* (2013.01); *A61K 31/4164* (2013.01); *A61K 31/43* (2013.01); *A61K 31/47* (2013.01); *A61K 31/5375* (2013.01); *A61K 31/545* (2013.01); *A61K 31/7056* (2013.01); *A61K 9/0034* (2013.01)

(58) Field of Classification Search
CPC .... A61K 9/0034; A61K 9/006; A61K 9/0056; A61K 31/43; A61K 31/7056; A61K 31/545; A61K 31/4164; A61K 31/196; A61K 31/47; A61K 31/167; A61K 31/245; A61K 31/5375; A61K 9/7007
See application file for complete search history.

(56) References Cited

U.S. PATENT DOCUMENTS

| | | | | |
|---|---|---|---|---|
| 4,529,601 A | * | 7/1985 | Broberg | A61K 31/165 424/47 |
| 5,466,465 A | * | 11/1995 | Royds | A61K 9/703 424/447 |
| 6,620,852 B2 | * | 9/2003 | Brogan | A61K 31/00 514/535 |
| 2003/0068378 A1 | * | 4/2003 | Chen | A61K 9/0007 424/486 |
| 2005/0014823 A1 | * | 1/2005 | Soderlund | A61K 9/0014 514/536 |

FOREIGN PATENT DOCUMENTS

WO   WO 2005018323   *   3/2005

* cited by examiner

*Primary Examiner* — Suzanne Ziska

(74) *Attorney, Agent, or Firm* — Joseph P. Kincart

(57) ABSTRACT

The present invention, as described above and as further defined by the claims, provides methods of administering an active agent via adhesion of a film to a mucous membrane in the oral cavity of a mammal, as well as and ODF formed therefore. An active agent may be ingested as the ODF dissolves resulting in systemic treatment of the mammal. In additional embodiments, an ODF may provide topical administration of an active agent.

21 Claims, 5 Drawing Sheets

301

302

VETERINARY ACTIVE AGENT APPLICATION

CROSS REFERENCE TO RELATED APPLICATIONS

The present application claims priority to U.S. Provisional Patent No. 61/806,779, entitled Veterinary Active Agent Application and U.S. patent application Ser. No. 13/732,408 entitled: Oral Anesthesia Application, and filed Jan. 1, 2013, as a Continuation in Part Application which claims priority to U.S. Provisional Patent Application No. 61/582,453, also entitled Oral Anesthesia Application the contents of which are relied upon and incorporated herein by reference.

The present invention relates to methods and apparatus for administering an active agent within an oral cavity of an animal. More specifically, the present invention presents methods and apparatus for applying a film including a medicament or other active agent to a gum or other mucous membrane of an animal.

BACKGROUND OF THE INVENTION

Giving an animal medication can be difficult. The animals conceptually don't understand that the medications will help them. Instead they see a pill as something to avoid eating. Industry and folk lore are filled with advice on how to administer a medicine to an animal. Family cats and dogs although generally eager to please may become very willful once they determine that they do not wish to swallow a medicine and squirm and refuse entry to their mouths. Farm animals, including bred horses and livestock may also resist ingestion of a medicine, even if they otherwise cooperate with their human caretakers. Wild animals have no particular desire to cooperate with human beings and may therefore be even more difficult. Classically pills have been covered with various foods to mask or trick the animal to ingesting it.

Other prior art includes such ineffectual methods such as placing a cat on the owners chest and removing the owners hands forcing the cat to hold on with its claws while the owner forces the medicine into the cats mouth; or filling a syringe or dropper with a fluid and squirting it into the animals mouth, only to have the animal spit it out. Another method is to hold the animal's muzzle, force the mouth open, place the medicine at the back of the throat and then hold the muzzle closed. This method is very difficult with large animals and often ends with the animal becoming stressed and spitting the medicine out.

What is needed therefore is a way to easily administer an active agent to animals in a manner that does not agitate the animal or induce pain to the animal and which also increases compliance of the animal.

SUMMARY OF THE INVENTION

Accordingly, the present invention provides methods and products for administering active agents to an animal via a mucous membrane. In particular, oral thin films are sized and shaped to adhere to areas of a mammalian gum and release an active agent to the area of the gum to which they are adhered. The oral thin films may include, for example, orally dissolving films (ODFs) which provide quick release of an active pharmaceutical ingredient (API) when placed on a moist mucosal surface. Placing an Active Pharmaceutical ingredient into a strip will make giving an animal medication easier. The hydrophilic nature of the strip makes it "stick" to anything wet. Examples of these include: Oral mucosa, tongue, moist food. Once the medication is stuck the animal cannot avoid ingesting it. The film can dissolve completely in fluids, so placing it into liquid is an additional delivery technique.

Preferably an orally dissolving thin film is mixed with a food flavoring for the animal, such as chicken or beef flavor and also combined with an active agent. When the dissolving film is placed on an animal's tongue or mucous membrane, the film adheres to the mucous membrane. The active agent will be released as the film dissolve and either be ingested and thereby administered systemically, or be absorbed through the mucous membrane.

Some embodiments of the present invention provide for rapid adherence of the film to mucosal tissue and direct administration of an anesthetic agent directly to the site of adherence. In general, the film is placed on a gum or other mucosal tissue and hydrated with saliva; the saliva hydration causes adherent forces to bind the specifically sized ODF on to a site of anesthetic application, or other delivery of an active agent. The anesthesia is administered directly into the adhesion site on the gum. As the ODF dissolves, traditional injected medicaments, such as an injection of pharmaceutical may be administered directly into the mucous membrane site that has been anesthetized by the anesthetic agent of the ODF.

DETAILED DESCRIPTION

Figure 1:
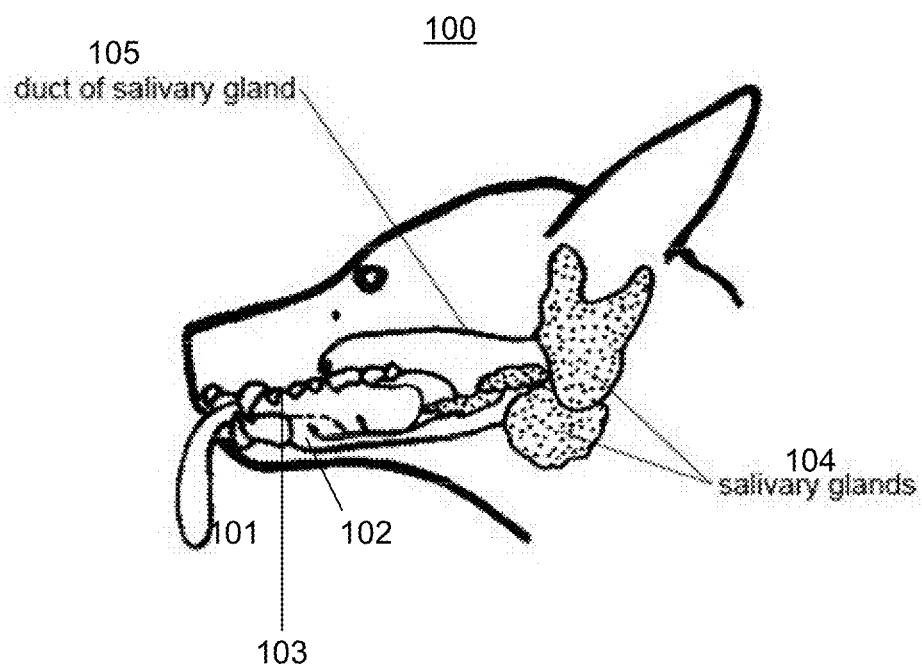
FIG. 1 illustrates an oral cavity in which the present invention may be implemented.

The present invention provides methods and products for locally administering one or more active agents via adhesion of a film to a mucous membrane such as, for example, mucous membrane included in a non-human mammalian oral cavity. A dissolving film containing an active agent is placed upon a mucous membrane, such as a membrane within the oral cavity. A hydrophilic nature of the dissolving film causes the film to stick to the mucous membrane. As the film dissolves, the active agent may either be ingested via the gastrointestinal tract or absorbed through the skin of the mucous membrane. The active agent may include, for example a medication for treating a condition present in the animal or to prophylactically treat the animal.

Specific examples of a medicament or active agent may include, by way of example, one or more of: Antibiotics (Amoxicillin Clindamycim, Clavamox, Tetracyclines, Baytril, Cephalexin, Metronidazole); Anti-inflammatories (Deramaxx, Rimadyl, Metacam, Prednisone); Anti-convulsants (Phenobarbital, Potassium Bromide, Valium); Flea treatments for treatment against fleas on a mammal (i.e. Advantage™, Frontline™, Advantix™); Heartworm Preventatives (Interceptor™, Heartgard™; Anti-allergy drugs (Prednisone™, Antihistamines™) Dewormers (Pyrantel Pamoate, Nemex, Strongid, Panacur, Droncit); Chemotherapeutic medications; Hormone replacement medications; and Antifungals.

Other examples, which include local aenesthetics may include, but are not limited to: benzocane, butamben, dibucaine, lidocaine, oxybuprocaine, pramoxine, proparacaine, proxymetacaine, and tetracaine (also named amethocaine).

Other exemplary areas of mammalian mucous membrane may include, but not be limited to a mammalian vaginal cavity. Other procedures may include a biopsy or other minor incision. A biopsy or incision may include, by way of example a cervical biopsy which may be painful without anesthesia.

Orally Dissolving Films (sometimes referred to herein as "ODF") as used herein shall mean a non-toxic film which may be placed in an mammalian oral cavity and dissolve as a result of contact with saliva or other liquid on of secreted by the mucous membrane comprising the mammalian oral cavity.

In various embodiments, ODFs may contain, by way of teaching example one or more of: film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

An ODF according to the present invention may additionally include supplementary ingredients such as, by way of example: plasticizers, sweetening and flavoring agents, coloring agents, saliva-stimulating agents, and thickening agents. Inactive ingredients of may include: Methocel K3, Methocek K100, Methocel K4, Sodium Carboxymethyl Cellulose, Glycerine, Sucralose, Polysorbate 80, Peppermint Oil Flavor, Gum Arabic, Sodium Copper Chlorophylin.

Oral Cavity Based Size and Shape (sometimes referred to herein as "OCBSS) as used herein shall mean a size and shape of an ODF suitable for placement on the surface of a mucous membrane and/or gum comprising a mammalian oral cavity.

An active agent or a medicament includes a substance that promotes recovery from injury or ailment. Active agents may include a pharmaceutical; drug; nutraceutical or nutritional aid; vitamin, herb or other substance administered to promote health.

Referring now to FIG. 1, a cutaway of a profile of a mammalian oral cavity 101 (as illustrated a canine oral cavity) is illustrated. The mammalian oral cavity 100 may be include for example by tongue 101, a gum 102, a palate 103, salivary glands 104 and a duct of salivary gland 105. The mammalian oral cavity will include mucosal membrane tissue 101-103 that is kept moist at least in part with saliva from the salivary glands.

Figure 2:
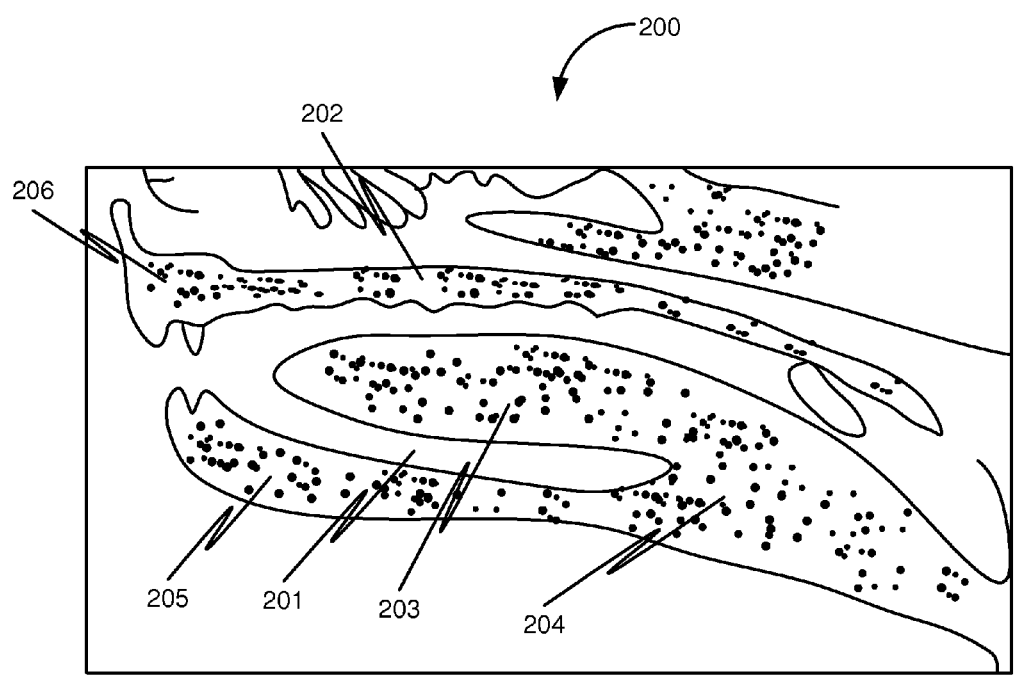
FIG. 2 illustrates a human upper gum and lower gum with locally administrating ODF strips according to some embodiments of the present invention.

Referring now to FIG. 2, a perspective view of a canine oral cavity 200 with ODF 201-206 placed upon mucous membrane is illustrated. As illustrated, the ODF 201-206 may be placed under the tongue 201, on the palate 202, on the tongue 203, on the gum in the lower rear of the cavity 204, on the lower gum in the frontal region 205, on the upper gum 206 are shown. As illustrated, some locations 201-202 and 204-206 have an oval shaped ODF placed on mucous membrane surface and a rectangular strip 203 is placed on the tongue.

Figure 3:
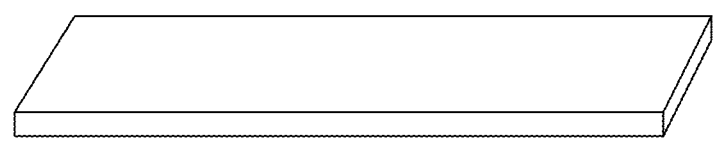
FIG. 3 illustrates rectangular shape and oval shape implementations according to some embodiments of the present invention.
Figure 3:
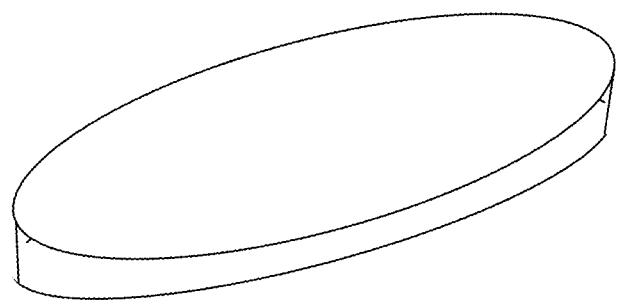

Referring now FIG. 3, perspective views of exemplary shapes of Oral Cavity Based Shapes are illustrated. Illustrated shapes include, by way of example, rectangular 301 and oval 302. Other shapes are also within the scope of the present invention. In some embodiments, an ODF may be one or both of: shaped and sized with a scissor prior to placement on a gum or mucous membrane. Placement may be accomplished via a human finger or a swab or other instrument.

Figure 4:
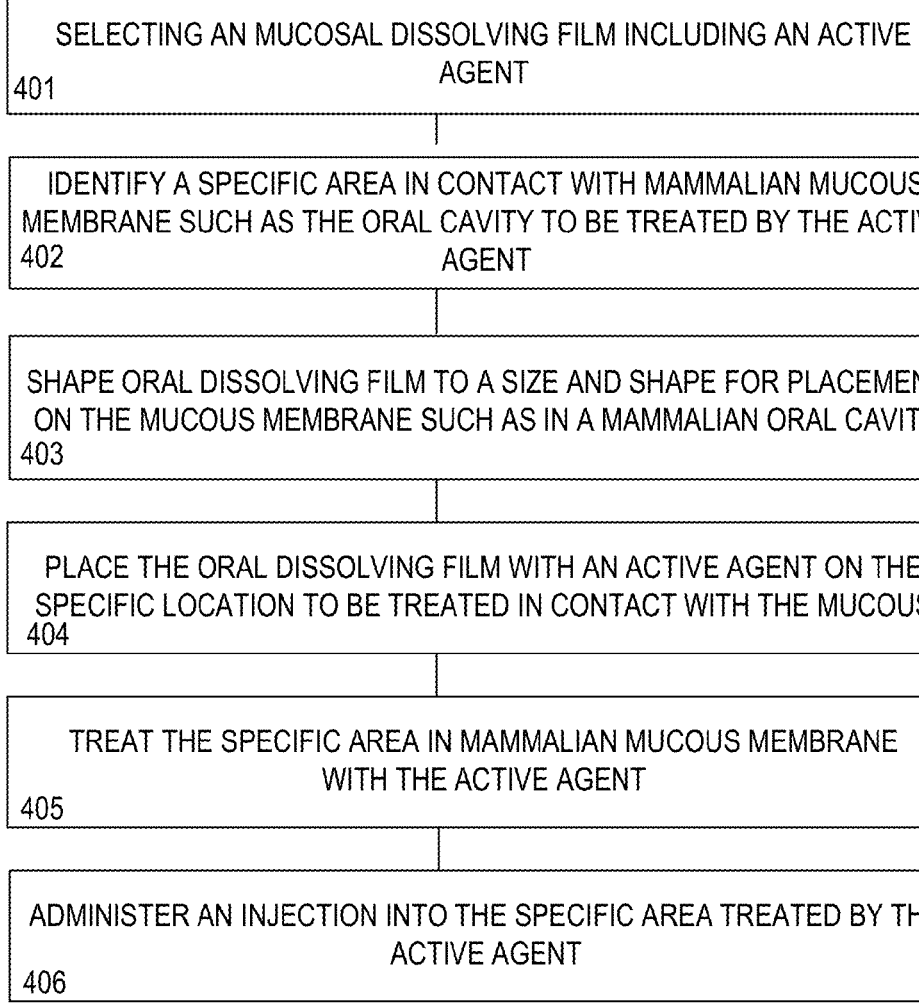
FIG. 4 illustrates method steps that may be practiced in some implementations of the present invention.

Referring now to FIG. 4, exemplary steps that may be practiced in some embodiments of the present invention are illustrated. The steps are presented in a logical order for some embodiments, however, the order presented is by way of example only and not meant to limit the scope of the invention. At 401, an active agent may be included in an ODF. At 402, a specific location or area within a mammalian cavity to be anesthetized or otherwise treated by an active agent included within the ODF. At 403, the ODF may be sized and shaped such that it is suitable for placement on the specific location or area identified. At 404, the ODF which has been shaped is placed at the desired location to be treated. At 405, the specific location or area in the mammalian oral cavity which be treated received the effect of the active agent.

At 406, in some embodiments, local treatment of mucous membrane may be followed with an injection administered into the treated area. An injection may include, for example, one or more of: a medicine, a pharmaceutical, an active agent, an anti-fungal, and additional anesthesia.

Accordingly, in various embodiments, an ODF may include an active agent that is a pharmaceutical ingredient. The pharmaceutical ingredient may be absorbed at the specified location for local oral administration as opposed to systemic active pharmaceutical ingredient.

According to some embodiments, the active pharmaceutical ingredients may include those known to topically treat oral conditions such as, by way of non-limiting example, one or more of: anesthetics, antifungal; antiseptics; and topical steroids.

According to the present invention, the nature of the film that is included in the ODF fixates the location of active pharmaceutical ingredient, eliminating migration, dissipation and dilution. The adhesion may be described as muco-adherence, wherein muco-adherence allows for a lower concentration of a given active pharmaceutical ingredient to be used to achieve a desired amount of anesthetic action and/or a desired health benefit.

Generally, lower concentration of an active agent may be beneficial due to a decrease in deleterious systemic side effects of excessive active pharmaceutical ingredient absorption such as methemaglobinemia or excessive exogenous steroids.

In some embodiments, and ODF may include a coloring agent to provide a visual indication of when the ODF dissolves and also a visual indication of which of the oral mucosa has been treated for easier identification of a treated area. Coloring agents may include, for example, a substance that allows a practitioner to identify an area that has been treated by an active agent, such as an anesthetic, whereby an injection may be administered into the area that has been made numb by anesthetic.

Coloring agents may include any benign coloring that is visible to a practitioner who will administer an injection. Accordingly, coloring agents may include by way of non-limiting example, natural pigments derived from natural sources such as vegetables, minerals or animals. Including: annatto, beet extract, caramel, beta-carotene and grape skin extract.

Other examples of coloring agents may include: Caramel coloring (E150), or other coloring made from caramelized sugar; Annatto (E160b), a reddish-orange dye or other coloring made from the seed of the achiote; Chlorophyllin (E140), a green dye or other coloring made from chlorella algae; Cochineal (E120), a red dye or other coloring derived from the cochineal insect, Dactylopius coccus; Betanin (E162) or other coloring extracted from beets; Turmeric or other coloring derived from curcuminoids, E100; Saffron or other coloring derived from carotenoids, E160a; Paprika (E160c); Lycopene (E160d); Elderberry juice; Pandan a green coloring or other coloring derived Pandanus amaryllifolius; Butterfly pea a blue dye or other coloring derived from *Clitoria ternatea.*

Other Coloring agents may include coloring approved under the Pure Food and Drug Act including, but not limited to: FD&C Blue No. 1—Brilliant Blue FCF, E133 (blue shade); FD&C Blue No. 2—Indigotine, E132 (indigo shade); FD&C Green No. 3—Fast Green FCF, E143 (turquoise shade); FD&C Red No. 40—Allura Red AC, E129 (red shade); FD&C Red No. 3—Erythrosine, E127 (pink shade, commonly used in glace cherries); FD&C Yellow No. 5—Tartrazine, E102 (yellow shade); and FD&C Yellow No. 6—Sunset Yellow FCF, E110 (orange shade).

In some preferred embodiments, the ODF with an active agent includes a film that is colored, so that when the ODF dissolves, the treated oral mucosa is easily identified.

The ODF may also be stored in aseptic packaging, limiting cross contamination and include flavoring which is pleasant to taste.

In some embodiments, exemplary ODFs may contain film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

Additional ingredients that may be included in various embodiments include one or more of: plasticizers, sweetening and flavoring agents, coloring agents, saliva-stimulating agents, and thickening agents. In some preferred embodiments, inactive ingredients may include: Methocel K3, Methocek K100, Methocel K4, Sodium Carboxymethyl Cellulose, Glycerine, Sucralose, Polysorbate 80, Peppermint Oil Flavor, Gum Arabic, and Sodium Copper Chlorophylin.

In some embodiments, an active agent may include an anesthetic that is administered prior to an injection. Specific examples include an active agent including ethyl ester of p-amino benzoic acid (PABA), such as, for example, benzocaine. Other examples may include, but are not limited to: benzocaine, butamben, dibucaine, lidocaine, oxybuprocaine, pramoxine, proparacaine, proxymetacaine, and tetracaine (also named amethocaine). A film with an active anesthetic agent is placed upon a mucous membrane and an area of the mucous membrane is anesthetized such that a procedure, including for example as an injection or an incision, may be administered to the anesthetized area.

In another aspect of the present invention, the ODF, may be stored in aseptic packing to limit cross contamination. The ODF may also be individually labeled to identify the contents and dosage.

Figure 5:
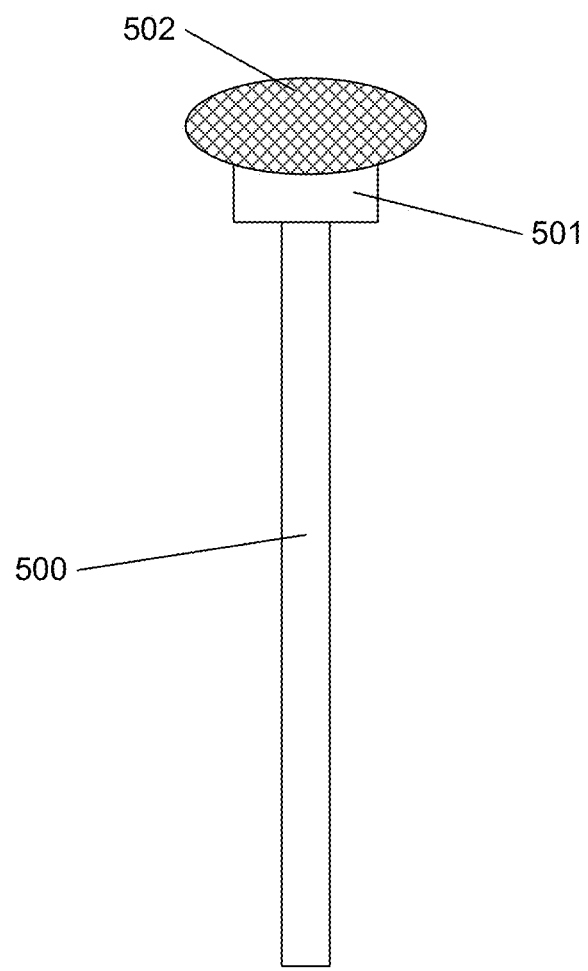
FIG. 5 illustrates an exemplary applicator according to some embodiments of the present invention.

Referring now toe FIG. 5, in some embodiments, an applicator 500 may also be used to assist in placing the ODF 502 within a area of an oral cavity with limited access. The ODF may be mounted on an application pad 501 and applied by swiping the ODF 502 over an area of the oral cavity that is moist. Aseptic packaging may enclose all of, or some portions of the entire applicator 500, including application pad 501 and ODF 502, the application pad 501 and ODF 502, or just the ODF 502.

An aseptic package may also be labeled to identify dosage and side affects. In some embodiments, the film itself may be printed upon to identify the active agent and dosage information.

Alternative administration may also include dissolving the film in food or water.

In still other embodiments, a film with an active agent may be placed upon a mucous membrane and an area of the mucous membrane is anesthetized so that a procedure, such as an injection or an incision, may be administered to the anesthetized area.

CONCLUSION

The present invention, as described above and as further defined by the claims below, provides methods of administering an active agent via adhesion of a film to a mucous membrane in the oral cavity of a mammal, as well as and ODF formed therefore. The exemplary style of describing is not meant to limit the scope of the invention and the invention is therefore more clearly described and limited by the claims below.

What is claimed is:

1. A method of applying an active agent to a specific site in a non-human mammalian oral cavity, the method comprising the steps of:
    selecting an oral dissolving film shaped to adhere to a non-human mammalian gum in an oral cavity, said oral dissolving film comprising the active agent and a coloring agent and capable of dissolving completely once exposed to saliva;
    identifying a specific area on a mucous membrane in the non-human mammalian oral cavity for adhesion of the oral dissolving film;
    placing the oral dissolving film comprising the active agent on the identified specific area of the mucous membrane;
    dissolving the oral dissolving film essentially in its entirety;
    generating a visual indicator on the identified area of the mucous membrane with the coloring agent, wherein the visual indicator remains on the mucous membrane following the dissolving of the oral dissolving film essentially in its entirety; and indicates that the active agent included in the film has been administered to the non-human mammal; and
    treating the non-human mammal with the active agent included in the oral dissolving film, wherein the treating the identified area includes one or both of ingestion of the active agent or topical absorption of the active agent.

2. The method of claim 1 wherein the identified area comprises gum tissue within a canine oral cavity.

3. The method of claim 1 wherein the active agent comprises an antibiotic.

4. The method of claim 3 wherein the active agent comprises one of more of: Amoxicillin, Clindamycin, Clavamox, Tetracyclines, Baytril, Cephalexin, Metronidazol.

5. The method of claim 1 wherein the active agent comprises ethyl ester of p-aminobenzoic acid.

6. The method of claim 5 wherein the active agent comprises a food flavoring.

7. The method of claim 1 wherein the active agent comprises one of more of: butamben, dibucaine, lidocaine, oxybuprocaine, pramoxine, proparacaine, tetracaine, and proxymetacaine.

8. The method of claim 1, wherein the active agent comprises a vitamin.

9. The method of claim 1, wherein the active agent comprises a nutraceutical.

10. The method of claim 1, wherein the active agent comprises a nutrient.

11. The method of claim 1, wherein the active agent comprises treatment against fleas on the mammal.

12. The method of claim 1, wherein the method additionally comprises the steps of:
identifying an area treated by the active agent via the coloring agent; and
further treating the identified area.

13. The method of claim 12 wherein the additional treatment comprises an injection into the colored mucous membrane.

14. The method of claim 12 wherein the coloring agent comprises one or more pigments derived from natural sources comprising one or more of: vegetables, minerals and animals.

15. The method of claim 12 wherein the coloring agent comprises one or more of: annatto, beet extract, caramel, beta-carotene, and grape skin extract.

16. The method of claim 12 wherein the coloring agent comprises one or more of Caramel coloring (E150); Annatto (E160b); coloring made from the seed of the achiote; Chlorophyllin (E140); a green dye made from *chlorella* algae; Cochineal (E120), a red dye derived from the cochineal insect; Dactylopius coccus; Betanin (E162); coloring derived from carotenoids; E160a; Paprika (E160c); Lycopene (E160d); Elderberry juice; coloring derived *Pandanus amaryllifolius*; Butterfly pea a blue dye; and coloring derived from *Clitoria ternatea*.

17. The method of claim 12 wherein the coloring agent comprises one or more artificial colorings.

18. The method of claim 16 wherein the coloring agent comprises one or more of: FD&C Blue No. 1—Brilliant Blue FCF, E131 (blue shade); FD&C Blue No. 2—Indigotine, E132 (indigo shade); FD&C Green No. 3—Fast Green FCF, E143 (turquoise shade); FD&C Red No. 40—Allura Red AC, E129 (red shade); FD&C Red No. 3—Erythrosine, E127 (pink shade, commonly used in glacé cherries); FD&C Yellow No. 5—Tartrazine, E102 (yellow shade); and FD&C Yellow No. 6—Sunset Yellow FCF, E110.

19. The method of claim 1 wherein the active agent comprises a heartworm preventative.

20. The method of claim 1 wherein the active agent comprises a deworming agent.

21. The method of claim 1 wherein the active agent comprises an anti-fungal agent.

* * * * *